US008681337B2

(12) United States Patent
Gordley

(10) Patent No.: US 8,681,337 B2
(45) Date of Patent: Mar. 25, 2014

(54) INDEPENDENT-BEAM GAS FILTER CORRELATION RADIOMETRY WITH FIELD-OF-VIEW MATCHING

(75) Inventor: Larry L Gordley, Grafton, VA (US)

(73) Assignee: G & A Technical Software, Inc., Newport News, VA (US)

( * ) Notice: Subject to any disclaimer, the term of this patent is extended or adjusted under 35 U.S.C. 154(b) by 193 days.

(21) Appl. No.: 13/442,950

(22) Filed: Apr. 10, 2012

(65) Prior Publication Data

US 2013/0265578 A1  Oct. 10, 2013

(51) Int. Cl.
*G01N 21/00* (2006.01)
(52) U.S. Cl.
USPC .................................. 356/437; 250/338.5
(58) Field of Classification Search
None
See application file for complete search history.

(56) References Cited

U.S. PATENT DOCUMENTS

| | | | | |
|---|---|---|---|---|
| 3,488,491 A | * | 1/1970 | Schuman | 250/345 |
| 3,735,127 A | * | 5/1973 | Astheimer | 250/346 |
| 4,788,428 A | * | 11/1988 | Metcalf et al. | 250/332 |
| 5,036,198 A | * | 7/1991 | Spaeth | 250/343 |
| 5,128,797 A | * | 7/1992 | Sachse et al. | 359/246 |
| 6,756,592 B1 | * | 6/2004 | Smith et al. | 250/338.5 |
| 6,803,577 B2 | * | 10/2004 | Edner et al. | 250/339.09 |
| 6,822,236 B1 | * | 11/2004 | Nelson et al. | 250/338.5 |
| 7,189,970 B2 | * | 3/2007 | Racca et al. | 250/338.5 |
| 7,423,756 B2 | * | 9/2008 | Gordley | 356/437 |
| 7,460,235 B2 | * | 12/2008 | Gordley | 356/437 |
| 7,855,367 B2 | * | 12/2010 | Tolton et al. | 250/338.5 |
| 7,884,937 B2 | * | 2/2011 | Prasad et al. | 356/437 |
| 8,158,944 B2 | * | 4/2012 | Tolton et al. | 250/338.5 |
| 8,198,589 B2 | * | 6/2012 | Tolton et al. | 250/338.5 |
| 8,289,518 B2 | * | 10/2012 | Gordley et al. | 356/437 |
| 8,379,208 B1 | * | 2/2013 | Simmons et al. | 356/437 |
| 8,548,271 B2 | * | 10/2013 | Grimberg | 382/294 |
| 8,599,367 B2 | * | 12/2013 | Canham | 356/5.01 |

* cited by examiner

*Primary Examiner* — Gordon J Stock, Jr.
(74) *Attorney, Agent, or Firm* — Peter J. Van Bergen

(57) ABSTRACT

A GFCR system includes gas cells disposed to receive light energy associated with a field-of-view of an atmospheric region. Each gas cell has contents selected from the group consisting of a vacuum and a gas of unique composition. For each of the gas cells, the light energy passed therethrough is spectrally affected by the contents thereof and then output therefrom as a spectrally-affected beam of light energy associated with the field-of-view. An optical system disposed between the gas cells and an optical detector images each spectrally-affected beam on a unique region of the optical detector. One or more processors generate matched portions of each spectrally-affected beam so-imaged on the optical detector where each such matched portion corresponds to an identical portion of the field-of-view. GFCR computations can then be performed using the matched portions.

24 Claims, 3 Drawing Sheets

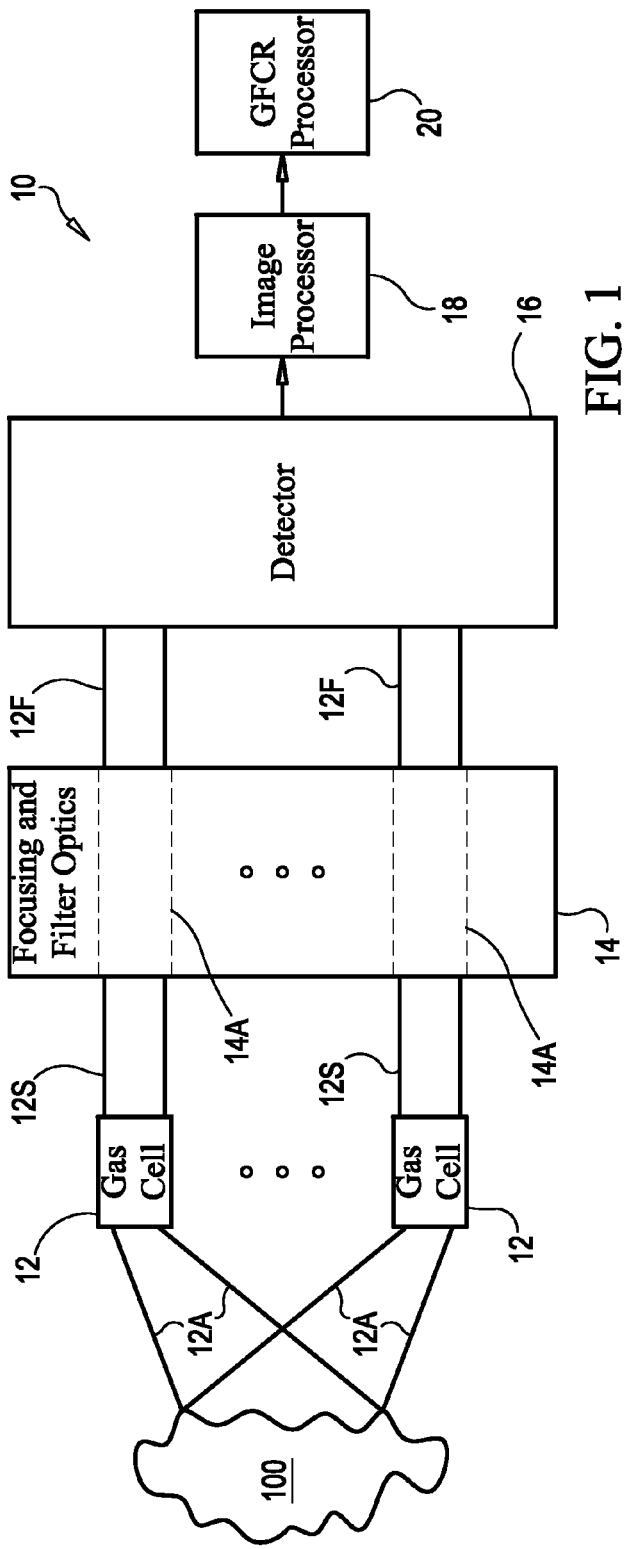
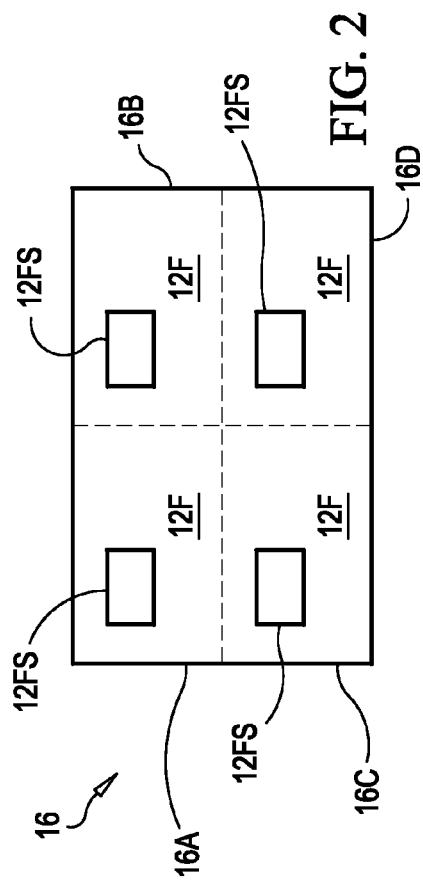

INDEPENDENT-BEAM GAS FILTER CORRELATION RADIOMETRY WITH FIELD-OF-VIEW MATCHING

FIELD OF THE INVENTION

The invention relates generally to Gas Filter Correlation Radiometry (GFCR) systems and methods, and more particularly to a GFCR system and method that independently views a scene of interest using multiple gas cells and then uses a single detector array and field-of-view matching for improved GFCR measurements.

BACKGROUND OF THE INVENTION

"Gas filter correlation radiometry" (GFCR) is an optical remote sensing method used to produce highly sensitive measurements of "targeted" gases. Conventional GFCR measurement systems have made use of multiple single-element detectors where each detector measures light energy passed through a gas cell of the GFCR system. For multi-path systems designed for spectral measurement simultaneity, the light energy is split (prior to impingement on the gas cells) into a number of optical paths commensurate with the number of gas cells in the GFCR system. Such GFCR systems can use "back-end" electrical components that include balancing electronics coupled to the outputs of the detectors. In practice, the detector signals are electronically or mathematically balanced to be approximately equal when viewing light from an unattenuated light source such as the sun observed above the atmosphere from a satellite. That is, the multiple detectors' signals are differenced and balanced to give nearly zero difference during solar observation above the atmosphere. The key to making these measurements is the ability to determine the balance and rate of change of the difference signal before the observation in order to mitigate error due to drifts in detector response. To achieve the desired measurement accuracy of 1 part in $10^4$ or greater, the balance must be known to $10^{-4}$ of the full broadband signal. Thus, small drifts in detector response, if not detected and corrected, can severely corrupt the difference measurement. However, because the conventional multiple-detector system/method requires continuous high-precision calibration of the balance condition (i.e. calibration of the signal drift due to changes in system response), many researchers abandoned the multiple-detector system/method in favor of single-detector, single-beam systems/methods that modulate the cell condition in some fashion.

Single-detector systems/methods can nearly eliminate detector instability as an error source by measuring both signals with the same detector. However, single-detector systems/methods present other technical hurdles depending on method of implementation. In one such single-detector system/method, the gas cell condition is modulated by changing pressure or optical mass thereby causing a significant decrease in sensitivity because the cell modulation produces a relatively small spectral difference between optical paths associated with the different gas cells. The signals are also difficult to model because of gas heating and cell state variation that may not reach uniform equilibrium. In addition, vibration and subtle optical changes can be problems for implementation requiring a steady field-of-view.

In another type of single-detector method/system, the light path is switched between a gas-cell path and a non-gas-cell (e.g., vacuum) path by either rapidly re-routing the beam (e.g., polarization switching techniques) or moving the gas cell into and out of the beam. However, both of these approaches introduce noise due to beam steering and loss of signal integration time due to time between modulated states, as well as subtle spectral response, polarization and field-of-view differences.

An even greater problem with any single-detector method/system is the loss of measurement simultaneity and/or the ability to exactly match field-of-views for gas and vacuum paths. That is, if the scene changes during the time necessary to switch between modulated states or because of field-of-view mismatch, the change in normalized difference signal (caused by scene brightness variation) will corrupt the data interpretation that assumes the difference signal is produced solely by spectral variation. For example, a satellite traveling at 7 km/sec encountering a 1% per kilometer change in mean scattering brightness over the field-of-view will experience a fractional brightness change of $10^{-4}$ in 1.4 milliseconds which could be falsely interpreted as spectral variation. This presents a severe problem for the single-detector method, or any method that does not make simultaneous and spatially identical measurements of the two states (i.e., gas path and vacuum path).

More recently, another single-detector system/method attempted to remedy the above-described problems by utilizing a two-beam approach that splits the light (beam) energy and forms two pupil images on the same two-dimensional detector array. See U.S. Pat. No. 7,460,235. While this patented approach solved the requirement of temporal simultaneity, some applications incurred small but unacceptable degrees of beam mismatch in terms of field-of-view, spectral response, polarization, and signal linearity.

SUMMARY OF THE INVENTION

Accordingly, it is an object of the present invention to provide a GFCR system and method capable of achieving measurement simultaneity for multiple gas cell paths.

Another object of the present invention is to provide a GFCR system and method that employs a single-array detector methodology.

Still another object of the present invention is to provide a GFCR system capable of achieving measurement simultaneity for multiple gas cell paths using a single detector while also simplifying calibration of the system.

Other objects and advantages of the present invention will become more obvious hereinafter in the specification and drawings.

In accordance with the present invention, a gas filter correlation radiometery (GFCR) system and method are provided. Each of a plurality of gas cells is disposed to receive light energy associated with a field-of-view of an atmospheric region. Each gas cell has contents selected from the group consisting of a vacuum and a gas of unique composition. For each of the gas cells, the light energy passed therethrough is spectrally affected by the contents thereof and then output therefrom as a spectrally-affected beam of light energy associated with the field-of-view. An optical system disposed between the gas cells and an optical detector images each spectrally-affected beam on a unique region of the optical detector. A processor (or processors) is used to generate matched portions of each spectrally-affected beam so-imaged on the optical detector where each of the matched portions corresponds to an identical portion of the field-of-view. GFCR computations can then be performed using the matched portions.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 1 is a schematic view of a "gas filter correlation radiometry" (GFCR) system employing independent beam viewing and field-of-view matching in accordance with an embodiment of the present invention;

FIG. 2 is a plan schematic view of a single detector illustrating four unique regions thereof in accordance with an embodiment of the present invention;

DETAILED DESCRIPTION OF THE INVENTION

Figure 3:
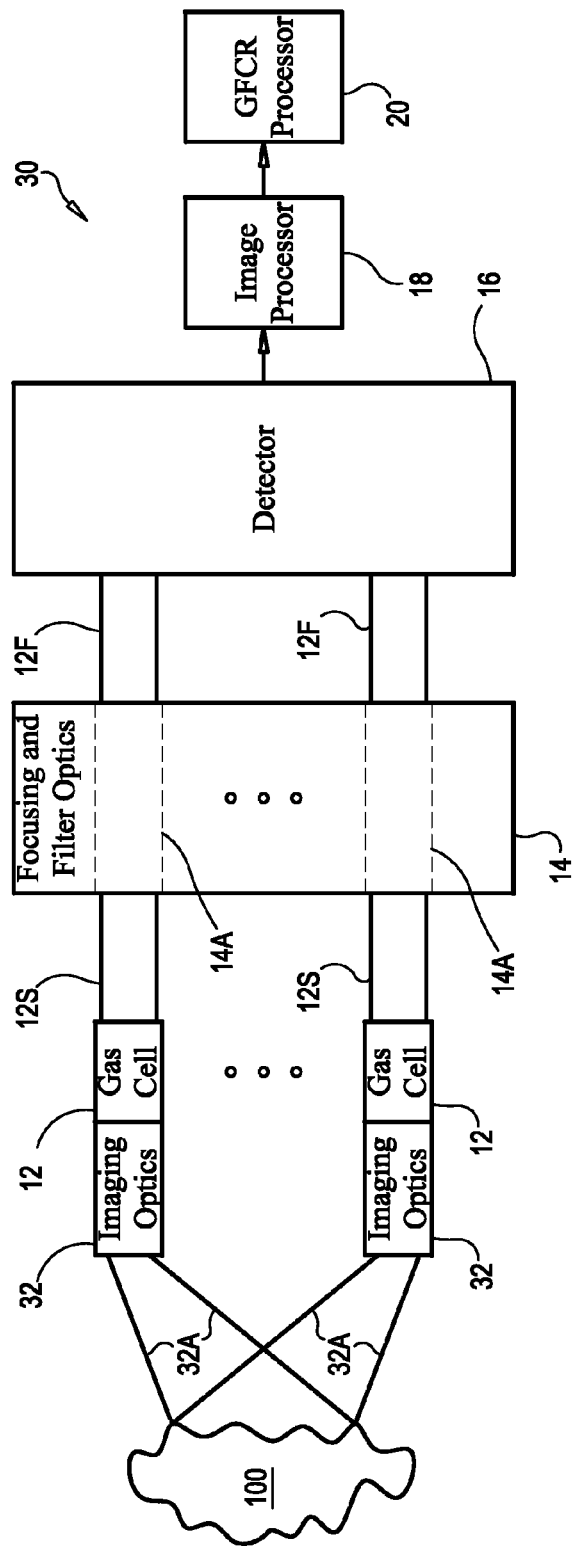
FIG. 3 is a schematic view of a GFCR system employing independent beam imaging/viewing and field-of-view matching in accordance with another embodiment of the present invention.

In general, a multi-beam "gas filter correlation radiometry" (GFCR) system images light onto a detector's focal plane after the light is split into separate optical paths with each such optical path including a gas cell through which the light passes. The present invention differs from previous GFCR multi-beam systems/methods in that the incoming light is not split into separate optical paths. Instead, independent beams are created with identical optical systems such that nearly identical far-field images are placed on the same two-dimensional detector focal plane array. Then, image processing techniques are applied to assure that truly identical far-field images are used for GFCR computation/processing.

Referring now to the drawings and more particularly to FIG. 1, a GFCR system in accordance with an embodiment of the present invention is shown and is referenced generally by numeral 10. A far-field location to be imaged/measured by GFCR system 10 is indicated by reference numeral 100. GFCR system 10 includes a number of gas cells 12, focusing and filter optics 14, a single optical detector 16 (e.g., a two-dimensional focal plane array of detector "pixels"), an image processor 18, and a GFCR processor 20. Processors 18 and 20 can be separate processors, can be combined into a single processor, and/or can be located locally or remotely with respect to the other elements of GFCR system 10 without departing from the scope of the present invention. The hardware used to implement the above-noted elements of GFCR system 10 would be understood by one ordinary skill in the art. However, it is the combination of the elements that define a novel GFCR system achieving measurement simultaneity and perfectly matched fields-of-view for multiple gas cell paths using a single detector.

The number of gas cells 12 used in GFCR system 10 can vary based on a given application. Generally, one of the gas cells 12 contains a vacuum with each other one of gas cells 12 containing a unique gas composition. The unique gas composition can include a target gas expected to be in the atmosphere between GFCR system 10 and far-field location 100. However, the present invention is not so limited as one or more of gas cells 12 can include a gas that excludes the atmospheric target gas of interest, but is partially correlated with light absorption features of the atmospheric target gas as described in pending U.S. patent application Ser. No. 12/931,075, the contents of which are hereby incorporated by reference. Therefore, in general, the gas cells can contain a variety of gases to provide filtering that induces a variety of spectral correlations with a variety of target gases or scene spectra.

Each gas cell 12 independently receives light energy associated with a common field-of-view imaged by the system. The field-of-view as seen by each gas cell 12 lies between view lines referenced by numerals 12A. As would be understood in the art, the light energy passing through each gas cell 12 is spectrally affected by the contents of the gas cell. As a result, a spectrally-affected beam 12S associated with a corresponding one of field-of-views 12A emerges from each gas cell 12.

Optics 14 "process" each spectrally-affected beam 12S identically and independently where such optics can include focusing optics, filtering optics, collimating optics, etc., typically found in GFCR systems. In one embodiment, optics 14 could comprise a plurality of independent and identical optical trains 14A with each such train being associated with a corresponding gas cell's spectrally-affected beam 12S. Ultimately, optics 14 produce a focused and collimated beam 12F for each corresponding spectrally-affected beam 12S. Each beam 12F is focused on a unique region of detector 16 thereby forming a corresponding image on detector 16. For example, a plan schematic view of detector 16 in FIG. 2 illustrates four regions 16A-16D (e.g., for a GFCR system 10 having four gas cells 12 where one gas cell contains a vacuum to define an unattenuated optical path and each of the other three gas cells contain a different gas composition). In this example, each unique region 16A-16D has a beam 12F focused thereon that corresponds to a particular one of the four gas cells. For purpose of this description, it will be assumed that each beam 12F fills a particular one of regions 16A-16D. The signal outputs generated by the pixels (not shown) in each region 16A-16D of detector 16 in response to being imaged by beams 12F are provided to image processor 18.

In the strictest sense, the field-of-view affected by each gas cell 12 will be unique owing to the minute variations of the gas cells and other optics, alignment errors, etc. The present invention eliminates the imaging imperfections that induce field-of-view mismatch through the image processing provided by image processor 18. Briefly, portions of the images formed on regions 16A-16D (i.e., sub-field-of-view images or sub-images 12FS as they will be referred to hereinafter) are defined for each region 16A-16D and matched by weighting pixel outputs. That is, by partitioning the detected images in each detector region into multiple sub-field-of-view images that tile the region, GFCR system 10 becomes an imaging system with a resolution consistent with either the angular width of the sub-field-of-view images 12FS or the optical resolution of the imaging system if it is wider than the physical size of the sub-image. The sets of identically matched sub-images 12FS (e.g., one set of four matched sub-images 12FS is illustrated in FIG. 2) can then be processed by GFCR processor 20. The particular type (or types) of GFCR processing applied to matched sub-images 12FS is not a limitation of the present invention.

The present invention creates matching sub-field-of-view images for multiple independent beams. Identical optical systems are used to place nearly identical images on the same detector. Then, sub-images are defined and their outputs are numerically matched by deriving coefficient sets for weighting pixel outputs that produce identical field-of-view responses. It is to be understood that there are many ways to derive these coefficients with commonly understood image analysis techniques such that their derivation is not a limitation of the present invention.

The present invention can also include "front end" optical components/systems to detect light energy in a selected fieldof-view. Accordingly, FIG. 3 illustrates another GFCR system 30 in accordance with the present invention where each gas cell 12 is preceded by imaging optics 32 (e.g. telescope, filters, polarizer's, etc.) where each such imaging optics 32 has the same structure/configuration and generates an independent field-of-view 32A. The remainder of GFCR system 30 operates as in the previously-described embodiment to generate matched sub-images for GFCR processing.

Figure 4:
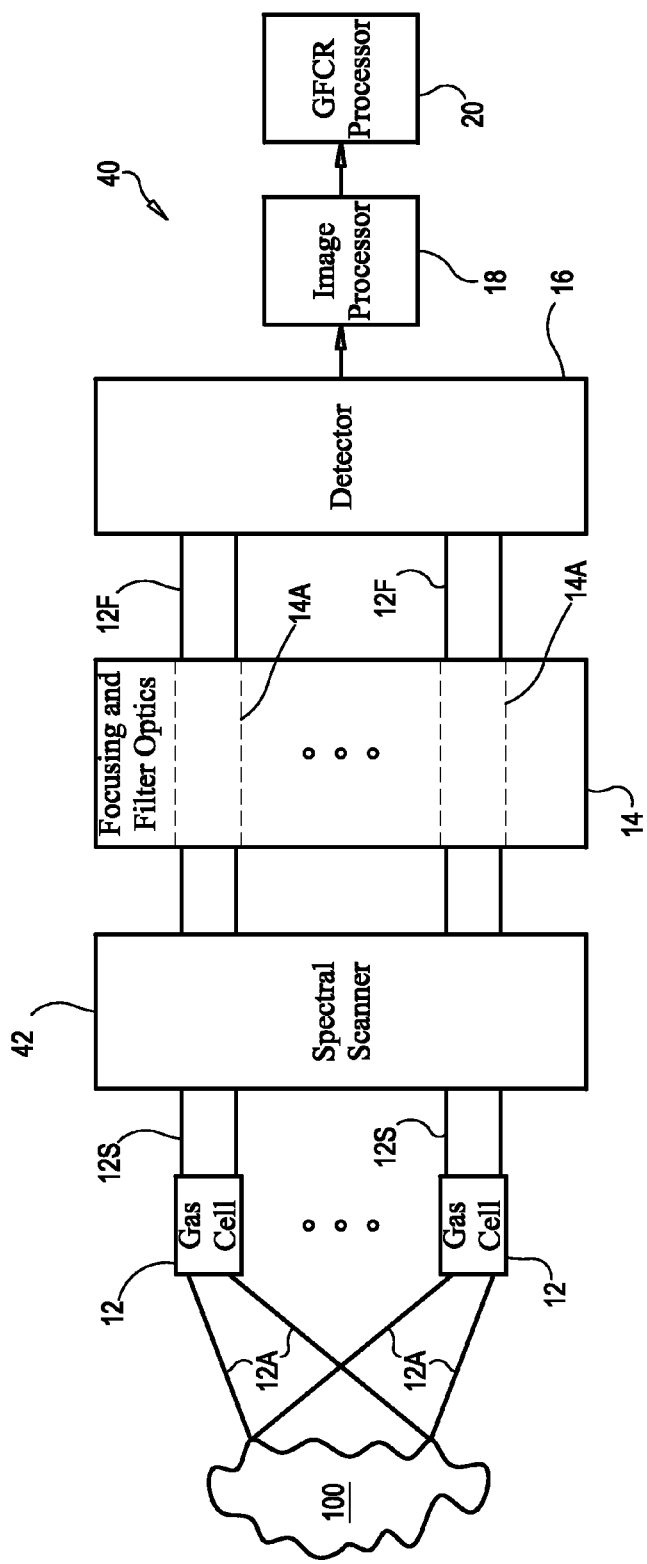
FIG. 4 is a schematic view of a GFCR system employing independent beam viewing, spectral scanning, and field-of-view matching in accordance with another embodiment of the present invention.

The present invention can incorporate a low resolution spectral scan for simplified and improved system calibration. Accordingly, FIG. 4 illustrates another GFCR system 40 in accordance with the present invention. In general, GFCR system 40 incorporates a low-resolution spectral scanner 42 to identically and simultaneously scan the spectral bandpass of all beams (or optical paths) passing through GFCR system 40 and prior to their impingement on detector 16. That is, all beams are scanned simultaneously with identical "scanning characteristics", i.e., using a spectral scanner with a resolution that is less or lower than the effective resolution of the gas cells' features. Scanner 42 can be realized in a variety of ways without departing from the scope of the present invention. For simplicity of construction, packaging and operation, scanner 42 can be implemented using individual and identical etalons that are temporally synchronized, or using one etalon intersecting all the beams, or some combination thereof. There are many ways to optically design GFCR system 40 to accomplish the above-defined simultaneous and identical low-resolution spectral scan to include placing scanner 42 (e.g., etalon(s)) in front of optics 14 (as shown), in front of gas cells 12, or in front of any imaging optics that might be placed in front of gas cells 12 (FIG. 3), provided the light is collimated when scanned by scanner 42. When an etalon(s) is used for scanner 42, the optical design used to achieve good quality and matching etalon effects in each beam is not a limitation of the present invention.

A low-resolution spectral/etalon scan as described above has several major advantages for the GFCR systems of the present invention. As is known in the art, a spectral scan by an etalon consists of a transmission "fringe" pattern that moves (i.e., actually stretches or contracts) spectrally. That is, "fringe" is a spectrally narrow transmission feature. During calibration of the present invention's GFCR systems, the scan spectra measured with and without a filled gas cell can be differenced and ultimately used to produce a normalized difference signal, M. The normalized difference signal, M, can be defined as:

$$M=(V_v-V_g)/V_{v0},$$

or $M=(V_v-V_g)/V_v=1-(V_g/V_v)$ depending on the application.

In these relationships, $V_{v0}$ is the vacuum path measurement without gas in the scene, $V_v$ is the vacuum cell beam signal, and $V_g$ is a filled cell signal, both with offsets removed and matching gains. Subscripts v and g indicate vacuum path and gas path respectively, and subscript 0 indicates an unattenuated scene (i.e., no atmosphere). The measured signals, $V_{vm}$ and $V_{gm}$, are:

$$V_{vm}=aV_v+V_{v,offset}$$

$$V_{gm}=bV_g+V_{g,offset}$$

where a and b are gain constants. The ratio a/b, and signal offsets $V_{v,offset}$ and $V_{g,offset}$ must be known in order to find M. These three values can be accurately determined from simulations of the low resolution spectra produced by the etalon scan, and fitting to the actual measurements. No-atmosphere measurements can be used for verifying cell content. To summarize, inclusion of the etalon scan feature in the present invention facilitates a complete calibration of the system to include offsets, response gain ratios, broad spectral bandpass, etalon scan spectral scale, fringe shape, and cell content.

Another advantage provided by etalon scanning is the creation of what will be referred to as "nano-channels". By differencing two normalized difference signals (i.e., the unattenuated "no atmosphere" scan and a normal scene scan), the transmission of the atmosphere at the cell line features can be inferred. Although the normalized difference signal will appear to consist of low resolution features, those features are in fact proportional to the spectral transmission as weighted by the cell gas absorption and the etalon fringe transmission multiplied by the broadband transmission. This is the equivalent of creating very narrow (i.e., spectral width of the cell absorption features) transmission filters that are referred to herein as nano-channels. The term "nano-channel" is chosen because the intrinsic resolution can be as much as 1000 times greater than the typical spectrometer measurement where the term "micro-channel" is generally used to describe spectral segments of spectrometer data. Thus, the inclusion of etalon(s) 42 allows each point on a difference signal feature to be a very high-resolution (or nano-channel) measurement.

The advantages of the present invention are numerous. The use of multiple independent beam views combined with field-of-view matching presents a precise GFCR measurement approach. The inclusion of etalon scanning provides a complete and accurate calibration method that can simultaneously produce moderate resolution spectra and nano-channels tailored to the application. Applications could vary from profile sounding to detection of anything with distinct spectral signature in the short-wave infra-red through thermal infra-red spectrums. The present invention is especially advantageous for use in applications requiring high spectral resolution. Instrumentation for most applications will be small and simple as compared to competing systems.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A gas filter correlation radiometery (GFCR) system, comprising:

a plurality of gas cells, each of said gas cells disposed to receive light energy associated with a common field-of-view of an atmospheric region, each of said gas cells having contents selected from the group consisting of a vacuum and a gas of unique composition wherein, for each of said gas cells, the light energy passed therethrough is spectrally affected by said contents thereof and then output therefrom as a spectrally-affected beam of light energy associated with said common field-of-view;

an optical detector;

an optical system disposed between said gas cells and said optical detector for imaging each said spectrally-affected beam on a unique region of said optical detector;

an image processor coupled to said optical detector for generating matched portions of each said spectrally-affected beam so-imaged on said optical detector wherein each of said matched portions corresponds to an identical portion of said common field-of-view; and a GFCR processor coupled to said image processor for performing GFCR computations using said matched portions.

2. A GFCR system as in claim 1, wherein said optical detector comprises a two-dimensional array of detector elements.

3. A system as in claim 1, wherein said optical system comprises a plurality of independent and identical optical trains wherein each of said optical trains is disposed between one of said gas cells and said optical detector.

4. A GFCR system as in claim 1, wherein said optical system includes at least one etalon filter for identically and simultaneously scanning a spectral bandpass of each said spectrally-affected beam.

5. A GFCR system as in claim 1, further comprising at least one etalon filter for identically and simultaneously scanning a spectral bandpass of the light energy prior to receipt thereof by said gas cells.

6. A GFCR system as in claim 4, wherein said at least one etalon filter comprises a plurality of temporally-synchronized etalon filters.

7. A GFCR system as in claim 5, wherein said at least one etalon filter comprises a plurality of temporally-synchronized etalon filters.

8. A gas filter correlation radiometry (GFCR) system, comprising:
a plurality of independent imaging optics, each of said imaging optics adapted to detect light energy associated with the same atmospheric field-of-view;
a plurality of gas cells in correspondence with said imaging optics, each of said gas cells disposed to receive the light energy so-detected by a corresponding one of said imaging optics, each of said gas cells having contents selected from the group consisting of a vacuum and a gas of unique composition wherein, for each of said gas cells, the light energy passed therethrough is spectrally affected by said contents thereof and then output therefrom as a spectrally-affected beam of light energy associated with said atmospheric field-of-view;
an optical detector;
optics disposed between said gas cells and said optical detector for imaging each said spectrally-affected beam on a unique region of said optical detector; and
at least one processor coupled to said optical detector for generating matched portions of each said spectrally-affected beam so-imaged on said optical detector wherein each of said matched portions corresponds to an identical portion of said atmospheric field-of-view, and for performing GFCR computations using said matched portions.

9. A GFCR system as in claim 8, wherein said optical detector comprises a two-dimensional array of detector elements.

10. A system as in claim 8, wherein said optics comprises a plurality of independent and identical optical trains wherein each of said optical trains is disposed between one of said gas cells and said optical detector.

11. A GFCR system as in claim 8, wherein said optics includes at least one etalon filter for identically and simultaneously scanning a spectral bandpass of each said spectrally-affected beam.

12. A GFCR system as in claim 8, further comprising at least one etalon filter for identically and simultaneously scanning a spectral bandpass of the light energy associated with said atmospheric field-of-view prior to receipt thereof by said gas cells.

13. A GFCR system as in claim 11, wherein said at least one etalon filter comprises a plurality of temporally-synchronized etalon filters.

14. A GFCR system as in claim 12, wherein said at least one etalon filter comprises a plurality of temporally-synchronized etalon filters.

15. A gas filter correlation radiometry (GFCR) system, comprising:
a plurality of gas cells, each of said gas cells disposed to receive light energy associated with a field-of-view of an atmospheric region, each of said gas cells having contents selected from the group consisting of a vacuum and a gas of unique composition wherein, for each of said gas cells, the light energy passed therethrough is spectrally affected by said contents thereof and then output therefrom as a spectrally-affected beam of light energy associated with said field-of-view;
a spectral scanner disposed to identically and simultaneously scan one of (i) a spectral bandpass of the light energy prior to receipt thereof by said gas cells, and (ii) a spectral bandpass of each said spectrally-affected beam;
an optical detector;
optics disposed between said gas cells and said optical detector for imaging each said spectrally-affected beam on a unique region of said optical detector; and
at least one processor coupled to said optical detector for generating matched portions of each said spectrally-affected beam so-imaged on said optical detector wherein each of said matched portions corresponds to an identical portion of said field-of-view, and for performing GFCR computations using said matched portions.

16. A GFCR system as in claim 15, wherein said optical detector comprises a two-dimensional array of detector elements.

17. A system as in claim 15, wherein said optics comprises a plurality of independent and identical optical trains wherein each of said optical trains is disposed between one of said gas cells and said optical detector.

18. A GFCR system as in claim 15, wherein said spectral scanner comprises at least one etalon filter.

19. A GFCR system as in claim 18, wherein said at least one etalon filter comprises a plurality of temporally-synchronized etalon filters.

20. A gas filter correlation radiometery (GFCR) method, comprising the steps of:
providing a plurality of gas cells, each of said gas cells disposed to receive light energy associated with a field-of-view of an atmospheric region, each of said gas cells having contents selected from the group consisting of a vacuum and a gas of unique composition wherein, for each of said gas cells, the light energy passed therethrough is spectrally affected by said contents thereof and then output therefrom as a spectrally-affected beam of light energy associated with said field-of-view;
focusing each said spectrally-affected beam on a unique region of an optical detector wherein a corresponding image is formed;
generating matched portions of each said image wherein each of said matched portions corresponds to an identical portion of said field-of-view; and
performing GFCR computations using said matched portions.

21. A method according to claim 20, further comprising the step of identically and simultaneously scanning a spectral bandpass of each said spectrally-affected beam.

22. A method according to claim 20, further comprising the step of identically and simultaneously scanning a spectral bandpass of the light energy prior to receipt thereof by said gas cells.

23. A method according to claim 20, wherein said optical detector comprises a two-dimensional array of detector elements.

24. A method according to claim 20, wherein said step of focusing is performed independently and identically for each said spectrally-affected beam.

* * * * *